US009546145B2

(12) United States Patent
Kurumatani et al.

(10) Patent No.: US 9,546,145 B2
(45) Date of Patent: Jan. 17, 2017

(54) COMBINATION THERAPY FOR THE TREATMENT OF CHRONIC RENAL FAILURE WITH AN ANGIOTENSIN II RECEPTOR ANTAGONIST AND BERAPROST

(75) Inventors: Hajimu Kurumatani, Kanagawa (JP); Mitsutaka Tamura, Kanagawa (JP)

(73) Assignee: Toray Industries, Inc. (JP)

(*) Notice: Subject to any disclaimer, the term of this patent is extended or adjusted under 35 U.S.C. 154(b) by 756 days.

(21) Appl. No.: 12/402,610

(22) Filed: Mar. 12, 2009

(65) Prior Publication Data

US 2009/0176848 A1 Jul. 9, 2009

Related U.S. Application Data

(62) Division of application No. 10/556,016, filed as application No. PCT/JP2004/006412 on May 6, 2004, now abandoned.

(30) Foreign Application Priority Data

May 9, 2003 (JP) ................................ 2003-131664

(51) Int. Cl.
A61K 31/343 (2006.01)
C07D 307/93 (2006.01)
A61K 31/4184 (2006.01)
A61K 31/5585 (2006.01)
A61K 45/06 (2006.01)

(52) U.S. Cl.
CPC ........... *C07D 307/93* (2013.01); *A61K 31/343* (2013.01); *A61K 31/4184* (2013.01); *A61K 31/5585* (2013.01); *A61K 45/06* (2013.01)

(58) Field of Classification Search
USPC ...................................................... 514/183
See application file for complete search history.

(56) References Cited

U.S. PATENT DOCUMENTS

| 4,472,384 | A | 9/1984 | Blaine et al. |
| 5,306,824 | A | 4/1994 | Powers et al. |
| 5,700,833 | A | 12/1997 | Watanabe et al. |
| 5,763,489 | A | 6/1998 | Taniguchi et al. |
| 5,854,281 | A | 12/1998 | Uekama et al. |
| 2003/0069221 | A1 | 4/2003 | Kosoglou et al. |
| 2003/0092760 | A1 | 5/2003 | Kurumatani et al. |
| 2004/0265238 | A1* | 12/2004 | Chaudry ........................ 424/45 |

FOREIGN PATENT DOCUMENTS

| EP | 0 084 856 A1 | 8/1983 |
| EP | 0 542 203 A2 | 5/1993 |
| EP | 0 548 959 A1 | 6/1993 |
| EP | 0 558 062 A2 | 9/1993 |
| EP | 0 578 847 A1 | 1/1994 |
| EP | 0 581 187 A1 | 2/1994 |
| EP | 1 013 639 A1 | 6/2000 |
| EP | 1 016 408 A1 | 7/2000 |
| EP | 1 106 176 A1 | 6/2001 |
| JP | 58-124778 A | 7/1983 |
| JP | 60-023324 A | 2/1985 |
| JP | 01-053672 B | 11/1989 |
| JP | 05-032602 A | 2/1993 |
| JP | 08-245498 A | 9/1996 |
| JP | 09-160320 | 6/1997 |
| JP | 11-189536 A | 7/1999 |
| JP | 2000-095770 A | 4/2000 |
| JP | 2000-191523 A | 7/2000 |
| JP | 3245864 B2 | 1/2002 |
| WO | 93/25574 A1 | 12/1993 |
| WO | 96/04248 A1 | 2/1996 |
| WO | 97/02032 A1 | 1/1997 |
| WO | 98/09949 A1 | 3/1998 |
| WO | 98/13356 A1 | 4/1998 |
| WO | 99/13880 A1 | 3/1999 |
| WO | 00/67748 A1 | 11/2000 |
| WO | 02/080929 A1 | 10/2002 |

OTHER PUBLICATIONS

Ono et al., Hemodynamic and hormonal effects of beraprost sodium, an orally active prostacylin analgoue, in patients with secondary precapillary pulmonary hypertension, 2003, Circulation Journal, vol. 67, pp. 375-378.*
Kincaid-Smith et al., Randomized controlled crossover study of the effect of proteinuria and blood pressure of adding an angiotensin II receptor antagonist to an angiotensin converting enzyme inhibitor in normotensive patients with chronic renal disease and proteinuria, 2002, Nephrol Dial Transplant, vol. 17, pp. 597-601.*
Matsuda et al., Differing Anti-Proteinuric Action of Candesartan and Losartan in Chronic Renal Failure, 2003, Hypertens Res, vol. 26, No. 11, pp. 875-880.*
Utsunomiya et al., Attenuation of immune complex nephritis in NZB/W F1 mice by a prostacyclin analogue, 1995, Clin. Exp. Immunol., vol. 99, pp. 454-460.*
Kushiro et al., Therapeutic effects of prostacyclin analog on crescentic glomerulonephritis of rat, 1998, Kidney International, vol. 53, pp. 1314-1320.*
Nakayama et al., Long-Term Renoprotective Effect of the Combination Therapy of ACE-inhibitor (ACE-I) and Prostaglandin E1 (PGE1) in Patients with Chronic Renal Failure (CRF), 2002, J Am Soc Nephrol, 13, PUB 164—Abstract Only.*
Imbs et al. "Clinical Pharmacology of Prostacylin and its Stable Analogs", 1991, Therapie, vol. 46, No. 3, pp. 211-116, Abstract Only.*
Lewis et al. Renoprotective effect of the angiotensin receptor antagonist irbesartan in patients with diabetic nephropathy due to type 2 diabetes, 2001, New England Journal of Medicine, vol. 345, No. 12, pp. 851-860.*
Wilkinson, A., "Use Angiotensin-Converting Enzyme Inhibitors and Angiotensin II Antagonists in Renal Transplantation: Delaying the Progression of Chronic Allograft Nephropathy" *Transplantation Review*, Jul. 2000, vol. 14, No. 3 pp. 138-144.
Villa, E. et al., "Effects of Cicaprost and Fosinopril on the Progression of Rat Diabetic Nephropathy," *American Journal Hypertension*, 1997, vol. 10, No. 2, pp. 202-208.
Kit E. Purdy et al., "Prostaglandins buffer ANG II-mediated increases in cytosolic calcium in preglomerular VSMC," Am. J. Physiol., 1999, vol. 277, pp. F850-F858.

* cited by examiner

*Primary Examiner* — James D Anderson
*Assistant Examiner* — Meghan Finn
(74) *Attorney, Agent, or Firm* — DLA Piper LLP (US)

(57) ABSTRACT

An agent for enhancing therapeutic or prophylactic effect of a renin-angiotensin system inhibitor on renal diseases is disclosed, including a specific prostaglandin I derivative such as beraprost sodium as an effective ingredient.

6 Claims, 2 Drawing Sheets

COMBINATION THERAPY FOR THE TREATMENT OF CHRONIC RENAL FAILURE WITH AN ANGIOTENSIN II RECEPTOR ANTAGONIST AND BERAPROST

RELATED APPLICATIONS

This application is a divisional of U.S. application Ser. No. 10/556,016, filed Nov. 8, 2005, which is a §371 of PCT/JP2004/006412, with an international filing date of May 6, 2004 (WO 2004/098611 A1, published Nov. 18, 2004), which is based on Japanese Patent Application No. 2003-131664, filed May 9, 2003.

TECHNICAL FIELD

This disclosure relates to a pharmaceutical for therapy or prophylaxis of renal diseases. More particularly, it relates to an agent for enhancing the therapeutic or prophylactic effect against renal diseases by administration of an inhibitor of the renin-angiotensin system.

BACKGROUND

In recent years, the number of patients suffering from nephropathy tends to increase. The reasons therefor include change in living environment, aging and increase in the number of patients suffering from diabetic nephropathy accompanied by the increase in the number of patients suffering from diabetes mellitus. The number of patients whose renal function decreased to reach renal failure so that dialysis is inevitable is increasing year by year. Dialysis treatment requires the patient to attend a hospital twice or thrice a week. In addition, dialysis treatment has a number of problems including disorder in production and maturation of erythrocytes; emergence of complications due to accumulation of aluminum or $\beta_2$-microglobulin accompanied by long-term dialysis treatment; and increase in pathologic change in cardiovascular system. Especially, in cases where the primary disease is diabetes mellitus, the survival rate after 5 years from the commencement of the dialysis treatment is as low as about 50%. Thus, a drug which suppresses the progress of renal diseases so as to extend the duration till the dialysis is strongly demanded.

To suppress progress of renal diseases, antihypertensive therapies are generally performed, in addition to diet therapies such as low protein diets. Moreover, in case of glomerulonephritis, steroid drugs or immunosuppressants are administered to suppress the inflammatory reaction, and in case of diabetic nephritis, insulin or oral antidiabetic agents are administered to attain strict control of blood glucose.

For patients who reached renal failure, drugs for suppressing increase in blood electrolytes are administered, and low protein diets are prescribed, in addition to the antihypertensive therapies. Further, in cases where renal anemia is complicated, erythropoietin is administered. Still further, to slow down the progression or to improve the uremia, oral adsorbent preparations may be used in some cases.

However, in spite of these therapies, the progression of renal failure cannot be well prevented at present.

Since renal diseases such as nephritis, diabetic nephropathy and renal failure often accompany hypertension, and since hypertension is thought to be one of the factors which aggravate the renal diseases, antihypertensive drugs are administered for the purpose of suppressing progress of the renal diseases. Among the antihypertensive drugs, inhibitors of the renin-angiotensin system are especially drawing attention. Angiotensin II having a high vasopressor activity is generated from angiotensin I by angiotensin converting enzyme (ACE). Therefore, substances which inhibit ACE have antihypertensive activities and are widely used as antihypertensive drugs. However, it is known that ACE inhibitors commonly have side effects such as dry cough. Another type of inhibitors of the renin-angiotensin system include angiotensin II receptor antagonists. The receptor of angiotensin II is known to include two subtypes, AT1 and AT2. Antagonists of AT1 receptor have been widely used as antihypertensive drugs having fewer side effects than ACE inhibitors.

It has been reported that ACE inhibitors and angiotensin II receptor antagonists suppress the progress of chronic glomerular nephritis and diabetic nephropathy in animal models and in human (Am J Med 1995 November; 99(5): 497-504, Diabetologia 1996 May; 39(5): 587-93, N Engl J Med 2001 Sep. 20; 345(12): 861-9, J Hypertens 1993 September; 11(9): 969-75). Further, it is thought that ACE inhibitors and angiotensin II receptor antagonists also have renal protective activities which are not related to the antihypertensive activities. For example, the effect of suppressing the progress of diabetic nephropathy by irbesartan was superior to that attained in cases where the blood pressure was controlled by a calcium antagonist (N Engl J Med 2001 Sep. 20; 345(12): 851-60). Therefore, particularly for the patients suffering from diabetic nephropathy, ACE inhibitors and angiotensin II receptor antagonists are widely used even if the blood pressure is within the normal range.

Thus, the usefulness of the inhibitors of the renin-angiotensin system such as ACE inhibitors and angiotensin II receptor antagonists against renal diseases are clinically well recognized.

However, it has been shown that the effects of suppressing progress of renal diseases by ACE inhibitors and angiotensin II receptor antagonists are limited. For example, in a clinical test of losartan which is a representative angiotensin II receptor antagonist, for patients suffering from diabetic nephropathy, it was proved that the doubling time of creatinine, the rate of cases where dialysis became necessary, and complicated risk of death were decreased. However, the risk-lowering rate was only 16.1% (N Engl J Med 2001 Sep. 20; 345(12): 861-9). The fact that the degree of suppression is not sufficient is evident from the fact that the number of patients who are newly required to receive dialysis exceeds 30,000 in Japan and is ever-increasing year by year, in spite of the fact that ACE inhibitors and angiotensin II receptor antagonists are widely used as antihypertensive drugs.

It has been reported that iloprost, a prostaglandin I derivative, decreased urinary protein in an anti-Thy1-induced nephritis model, which is a glomerular nephritis model (Am J Pathol 1993 February; 142(2): 441-50). Further, beraprost sodium, a prostaglandin I derivative, decreases urinary protein in glomerular nephritis model in rats (Kidney Int 1998 May; 53(5) 1314-20) and in patients suffering from diabetic nephropathy (Nephron 2002 December; 92(4): 788-96). Still further, it has been reported that cicaprost suppressed the diabetic nephritis induced by streptozotocin in rats (J Hypertens Suppl 1993 December; 11 Suppl 5: S208-9) and the renal dysfunction induced by uninephrectomy and by loading high sodium and high protein (Am J Hypertens 1997 10: 209-16).

WO 00/67748 discloses that m-phenylene $PGI_2$ derivatives including beraprost sodium are effective for the therapy of renal failure. WO 99/13880 discloses that m-phenylene $PGI_2$ derivatives including beraprost sodium are effective for nephritis, glomerular nephritis and diabetic nephropathy.

WO 02/080929 discloses that m-phenylene PGI$_2$ derivatives including beraprost sodium are effective for interstitial nephritis.

However, those publications merely disclose the effect of the prostaglandin I derivatives against the progress of nephropathy when administered individually, and the references are totally silent about the combination of prostaglandin I derivative and an inhibitor of the renin-angiotensin system.

A novel composition containing inter-phenylene-9-thia-11-oxo-12-azaprostanoic acid which is a novel compound of the prostanoic acid type, which has a special structure different from the native form, and an inhibitor of angiotensin converting enzyme. This reference discloses that these compounds have very strong vasodilating activities for renal blood vessels. However, the compound disclosed in this patent literature is different from prostaglandins, and the patent literature is totally silent about whether the compound enhances the suppressive effect of the inhibitors of the renin-angiotensin system against renal diseases (Japanese Laid-open Patent Application (Kokai) No. 60-23324).

Further, cicaprost, a prostaglandin I derivative, and fosinopril, an ACE inhibitor, were administered in combination to diabetes mellitus model in rats, and the progression of the diabetic nephropathy was evaluated (Am J Hypertens 1997 10: 202-208). In this literature, it is described that when each drug was administered individually, the renal function parameters such as urinary protein were less severe and the damage of renal tissue was lighter than the control group, but in cases where both of the drugs were administered in combination, the effect was not more than that attained in cases where each drug was administered individually, so that no synergistic effect was observed.

It could therefore be helpful is to provide an agent for enhancing therapeutic or prophylactic effect of administering renin-angiotensin system inhibitor on renal diseases.

SUMMARY

We discovered that particular prostaglandin I derivatives significantly and characteristically enhance the effect of renin-angiotensin system inhibitors to suppress progression of renal disease, thereby completing this disclosure.

That is, we provide an agent for enhancing therapeutic or prophylactic effect of administering (a) renin-angiotensin system inhibitor(s) on (a) renal disease(s), comprising as an effective ingredient a prostaglandin I derivative represented by the Formula (I):

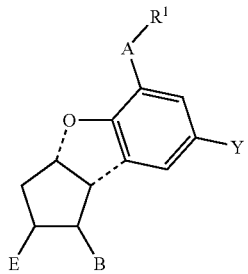

(I)

wherein $R^1$ is
(A) COOR$^2$, wherein $R^2$ is
1) hydrogen or a pharmaceutically acceptable cation,
2) $C_1$-$C_{12}$ straight alkyl or $C_3$-$C_{14}$ branched alkyl,
3) Z—R$^3$, wherein Z is covalent bond, or straight or branched alkylene represented by $C_tH_{2t}$, wherein t is an integer of 1 to 6, $R^3$ is $C_3$-$C_{12}$ cycloalkyl or $C_3$-$C_{12}$ cycloalkyl substituted with 1 to 3 $R^4$(s) wherein $R^4$ is hydrogen or $C_1$-$C_5$ alkyl,
4) —(CH$_2$CH$_2$O)$_n$CH$_3$, wherein n is an integer of 1 to 5,
5) —Z–Ar$^1$, wherein Z represents the same meanings described above, Ar$^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein the substituent(s) is(are) at least one of chlorine, bromine, fluorine, iodine, trifluoromethyl, $C_1$-$C_4$ alkyl, nitro, cyano, methoxy, phenyl, phenoxy, p-acetamidebenzamide, —CH=N—NH—C(=O)—NH$_2$, —NH—C(=O)-Ph, —NH—C(=O)—CH$_3$ and —NH—C(=O)—NH$_2$),
6) —C$_t$H$_{2t}$COOR$^4$, wherein $C_tH_{2t}$ and $R^4$ represent the same meanings as described above,
7) —C$_t$H$_{2t}$N(R$^4$)$_2$, wherein $C_tH_{2t}$ and $R^4$ represent the same meanings as described above,
8) —CH(R$^5$)—C—(=O)—R$^6$, wherein $R^5$ is hydrogen or benzoyl, and $R^6$ is phenyl, p-bromophenyl, p-chlorophenyl, p-biphenyl, p-nitrophenyl, p-benzamidephenyl or 2-naphthyl,
9) —C$_p$H$_{2p}$—W—R$^7$, wherein W is —CH=CH—, —CH=CR$^7$— or —C≡C—, wherein $R^7$ is hydrogen, $C_1$-$C_{30}$ straight or branched alkyl or $C_1$-$C_{30}$ aralkyl, p is an integer of 1 to 5, or
10) —CH(CH$_2$OR$^8$)$_2$, wherein $R^8$ is $C_1$-$C_{30}$ alkyl or acyl,
(B) —CH$_2$OH,
(C) —C(=O)N(R$^9$)$_2$, wherein $R^9$ is hydrogen, $C_1$-$C_{12}$ straight alkyl, $C_3$-$C_{12}$ branched alkyl, $C_3$-$C_{12}$ cycloalkyl, $C_4$-$C_{13}$ cycloalkylalkyene, phenyl, substituted phenyl (wherein the definitions of the substituent(s) are the same as those described in (A) 5) mentioned above), $C_7$-$C_{12}$ aralkyl or —SO$_2$R$^{10}$ wherein $R^{10}$ is $C_1$-$C_{10}$ alkyl, $C_3$-$C_{12}$ cycloalkyl, phenyl, substituted phenyl (wherein the definition(s) of the substituent(s) is(are) the same as those described in (A) 5) mentioned above), or $C_7$-$C_{12}$ aralkyl, wherein the two $R^9$s may be the same or different, with the proviso that when one of them is —SO$_2$R$^{10}$, the other $R^9$ is not —SO$_2$R$^{10}$, or
(D) —CH$_2$OTHP (wherein THP is tetrahydropyranyl),
A is
1) —(CH$_2$)$_m$—,
2) —CH=CH—CH$_2$—,
3) —CH$_2$—CH=CH—,
4) —CH$_2$—O—CH$_2$—,
5) —CH=CH—,
6) —O—CH$_2$— or
7) —C≡C—, wherein m is an integer of 1 to 3,
Y is hydrogen, $C_1$-$C_4$ alkyl, chlorine, bromine, fluorine, formyl, methoxy or nitro,
B is —X—C(R$^{11}$)(R$^{12}$)OR$^{13}$, wherein $R^{11}$ is hydrogen or $C_1$-$C_4$ alkyl, $R^{13}$ is hydrogen, $C_1$-$C_{14}$ acyl, $C_6$-$C_{15}$ aroyl, tetrahydropyranyl, tetrahydrofuranyl, 1-ethoxyethyl or t-butyl,
X is
1) —CH$_2$—CH$_2$—
2) —CH=CH— or
3) —C≡C—,
$R^{12}$ is
1) $C_1$-$C_{12}$ straight alkyl, $C_3$-$C_{14}$ branched alkyl,
2) —Z—Ar$^2$, wherein Z represents the same meanings as described above, Ar$^2$ is phenyl, α-naphthyl, β-naphthyl, or phenyl substituted with at least one of chlorine, bromine, fluorine, iodine, trifluoromethyl, $C_1$-$C_4$ alkyl, nitro, cyano, methoxy, phenyl and phenoxy,
3) —$C_tH_{2t}OR^{14}$, wherein $C_tH_{2t}$ represents the same meanings as described above, $R^{14}$ is $C_1$-$C_6$ straight alkyl, $C_3$-$C_6$ branched alkyl, phenyl, phenyl substituted with at least one of chlorine, bromine, fluorine, iodine, trifluoromethyl, $C_1$-$C_4$ alkyl, nitro, cyano, methoxy, phenyl or phenoxy-substituted phenyl, cyclopentyl, cyclohexyl, cyclopentyl substituted with 1 to 4 $C_1$-$C_4$ straight alkyl and cyclohexyl substituted with 1 to 4 $C_1$-$C_4$ straight alkyl,
4) —Z—$R^3$, wherein Z and $R^3$ represent the same meanings as mentioned above,
5) —$C_tH_{2t}$—CH=C($R^{15}$)$R^{16}$, wherein $C_tH_{2t}$ represents the same meanings as mentioned above, $R^{15}$ and $R^{16}$ represent hydrogen, methyl, ethyl, propyl or butyl, or
6) —$C_uH_{2u}$—C≡C—$R^{17}$, wherein u is an integer of 1 to 7, $C_uH_{2u}$ is straight or branched alkylene, and $R^{17}$ is $C_1$-$C_6$ straight alkyl,
E is hydrogen or —$OR^{18}$, wherein $R^{18}$ is $C_1$-$C_{12}$ acyl, $C_7$-$C_{15}$ aroyl or $R^2$ (wherein $R^2$ represents the same meanings as described above),
the formula includes d-isomers, 1-isomers and racemic compounds.

We also provide a therapeutic or prophylactic agent for renal disease, comprising as effective ingredients the above-described enhancing agent and a renin-angiotensin system inhibitor.

We further provide a kit for therapy or prophylaxis for renal diseases, comprising separately the above-described enhancing agent, and a drug containing as an effective ingredient a renin-angiotensin system inhibitor, wherein the kit is for administering the enhancing agent and the renin-angiotensin system inhibitor at the same time or at different times.

That is, we provide a method for enhancing therapeutic or prophylactic effect of a renin-angiotensin system inhibitor on renal disease including administering an enhancing agent including as an effective ingredient a prostaglandin I derivative represented by the Formula (I):

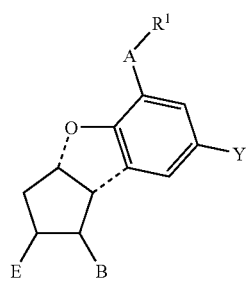

(I)

wherein $R^1$ is
(A) $COOR^2$, wherein $R^2$ is
1) hydrogen or a pharmaceutically acceptable cation,
2) $C_1$-$C_{12}$ straight alkyl or $C_3$-$C_{14}$ branched alkyl,
3) Z—$R^3$, wherein Z is covalent bond, or straight or branched alkylene represented by $C_tH_{2t}$ wherein t is an integer of 1 to 6, $R^3$ is $C_3$-$C_{12}$ cycloalkyl or $C_3$-$C_{12}$ cycloalkyl substituted with 1 to 3 $R^4$(s) wherein $R^4$ is hydrogen or $C_1$-$C_5$ alkyl,
4) —($CH_2CH_2O$)$_n$$CH_3$, wherein n is an integer of 1 to 5,
5) —Z—$Ar^1$, wherein Z represents the same meanings described above, $Ar^1$ is phenyl, α-naphthyl, β-naphthyl, 2-pyridyl, 3-pyridyl, 4-pyridyl, α-furyl, β-furyl, α-thienyl, β-thienyl or substituted phenyl (wherein the substituent(s) is(are) at least one of chlorine, bromine, fluorine, iodine, trifluoromethyl, $C_1$-$C_4$ alkyl, nitro, cyano, methoxy, phenyl, phenoxy, p-acetamidebenzamide, —CH=N—NH—C(=O)—$NH_2$, —NH—C(=O)-Ph, —NH—C(=O)—$CH_3$ and —NH—C(=O)—$NH_2$),
6) —$C_tH_{2t}COOR^4$, wherein $C_tH_{2t}$ and $R^4$ represent the same meanings as described above,
7) —$C_tH_{2t}N(R^4)_2$, wherein $C_tH_{2t}$ and $R^4$ represent the same meanings as described above,
8) —CH($R^5$)—C—(=O)—$R^6$, wherein $R^5$ is hydrogen or benzoyl, and $R^6$ is phenyl, p-bromophenyl, p-chlorophenyl, p-biphenyl, p-nitrophenyl, p-benzamidephenyl or 2-naphthyl,
9) —$C_pH_{2p}$—W—$R^7$, wherein W is —CH=CH—, —CH=$CR^7$— or —C≡C—, wherein $R^7$ is hydrogen, $C_1$-$C_{30}$ straight or branched alkyl or $C_1$-$C_{30}$ aralkyl, p is an integer of 1 to 5, or
10) —CH($CH_2OR^8$)$_2$, wherein $R^8$ is $C_1$-$C_{30}$ alkyl or acyl,
(B) —$CH_2OH$,
(C) —C(=O)N($R^9$)$_2$, wherein $R^9$ is hydrogen, $C_1$-$C_{12}$ straight alkyl, $C_3$-$C_{12}$ branched alkyl, $C_3$-$C_{12}$ cycloalkyl, $C_4$-$C_{13}$ cycloalkylalkyene, phenyl, substituted phenyl (wherein the definitions of the substituent(s) are the same as those described in (A) 5) mentioned above), $C_7$-$C_{12}$ aralkyl or —$SO_2R^{10}$ wherein $R^{10}$ is $C_1$-$C_{10}$ alkyl, $C_3$-$C_{12}$ cycloalkyl, phenyl, substituted phenyl (wherein the definition(s) of the substituent(s) is(are) the same as those described in (A) 5) mentioned above), or $C_7$-$C_{12}$ aralkyl, wherein the two $R^9$s may be the same or different, with the proviso that when one of them is —$SO_2R^{10}$, the other $R^9$ is not —$SO_2R^{10}$, or
(D) —$CH_2OTHP$ (wherein THP is tetrahydropyranyl),
A is
1) —($CH_2$)$_m$—,
2) —CH=CH—$CH_2$—,
3) —$CH_2$—CH=CH—,
4) —$CH_2$—O—$CH_2$—,
5) —CH=CH—,
6) —O—$CH_2$— or
7) —C≡C—, wherein m is an integer of 1 to 3,
Y is hydrogen, $C_1$-$C_4$ alkyl, chlorine, bromine, fluorine, formyl, methoxy or nitro,
B is —X—C($R^{11}$)($R^{12}$)$OR^{13}$, wherein $R^{11}$ is hydrogen or $C_1$-$C_4$ alkyl, $R^{13}$ is hydrogen, $C_1$-$C_{14}$ acyl, $C_6$-$C_{15}$ aroyl, tetrahydropyranyl, tetrahydrofuranyl, 1-ethoxyethyl or t-butyl,
X is
1) —$CH_2$—$CH_2$—
2) —CH=CH— or
3) —C≡C—,
$R^{12}$ is
1) $C_1$-$C_{12}$ straight alkyl, $C_3$-$C_{14}$ branched alkyl,
2) —Z—$Ar^2$, wherein Z represents the same meanings as described above, $Ar^2$ is phenyl, α-naphthyl, β-naphthyl, or phenyl substituted with at least one of chlorine, bromine, fluorine, iodine, trifluoromethyl, $C_1$-$C_4$ alkyl, nitro, cyano, methoxy, phenyl and phenoxy,
3) —$C_tH_{2t}OR^{14}$, wherein $C_tH_{2t}$ represents the same meanings as described above, $R^{14}$ is $C_1$-$C_6$ straight alkyl, $C_3$-$C_6$ branched alkyl, phenyl, phenyl substituted with at least one of chlorine, bromine, fluorine, iodine, trifluoromethyl, $C_1$-$C_4$ alkyl, nitro, cyano, methoxy, phenyl or phenoxy-substituted phenyl, cyclopentyl, cyclohexyl, cyclopentyl substituted with 1 to 4 $C_1$-$C_4$ straight alkyl and cyclohexyl substituted with 1 to 4 $C_1$-$C_4$ straight alkyl, 4) —Z—$R^3$, wherein Z and $R^3$ represent the same meanings as mentioned above, 5) —$C_tH_{2t}$—CH=C($R^{15}$)$R^{16}$, wherein $C_tH_{2t}$ represents the same meanings as mentioned above, $R^{15}$ and $R^{16}$ represent hydrogen, methyl, ethyl, propyl or butyl, or 6) —$C_uH_{2u}$—C≡C—$R^{17}$, wherein u is an integer of 1 to 7, $C_uH_{2u}$ is straight or branched alkylene, and $R^{17}$ is $C_1$-$C_6$ straight alkyl, E is hydrogen or —$OR^{18}$, wherein $R^{18}$ is $C_1$-$C_{12}$ acyl, $C_7$-$C_{15}$ aroyl or $R^2$ (wherein $R^2$ represents the same meanings as described above), the formula includes d-isomers, l-isomers and racemic compounds to a patient to whom a renin-angiotensin system inhibitor(s) is(are) administered.

We also provide a method for treating or preventing a renal disease, comprising administering the above-described therapeutic or prophylactic agent for renal diseases, or the drugs contained in the above-described kit of therapeutic or prophylactic agents for renal diseases. We further provide use of the prostaglandin I derivative represented by the above-described Formula (I), for the production of an agent for enhancing the therapeutic or prophylactic effect of administering the renin-angiotensin system inhibitor on renal diseases.

We proved that the excellent effect of the renin-angiotensin system inhibitors to suppress progression of renal diseases is enhanced. Therefore, the dosages of the drugs necessary for obtaining the prescribed effects may be decreased, so that the side effects of the both drugs may be decreased and the compliance in taking these drugs may be promoted. Further, renal diseases for which the effects of the conventional renin-angiotensin system inhibitors are not sufficient may be effectively and safely treated.

DETAILED DESCRIPTION

Figure 1:
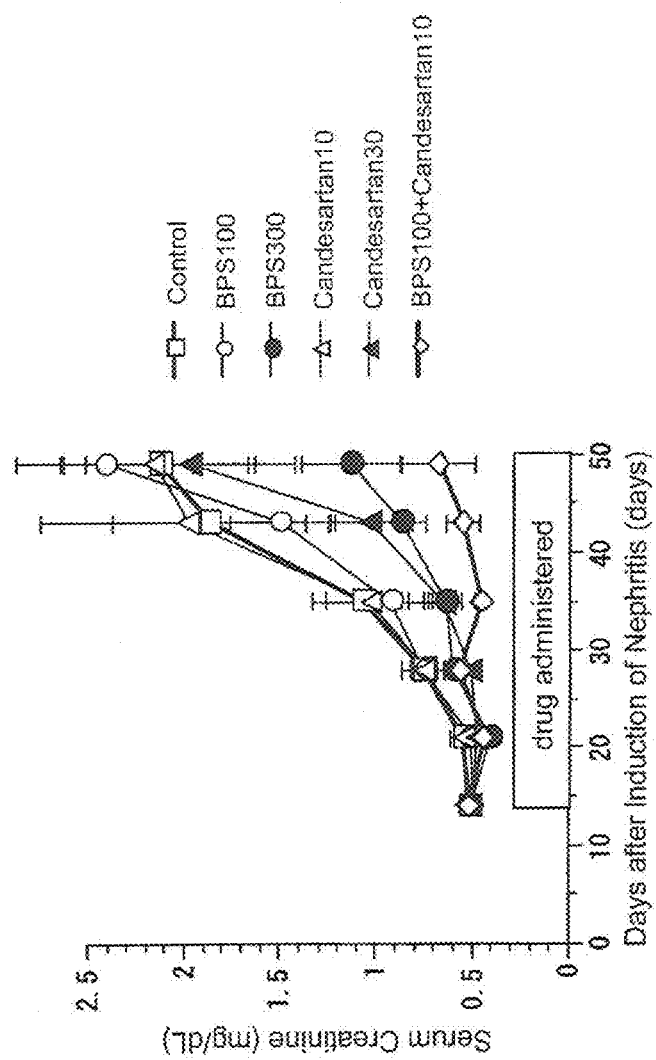
FIG. 1 shows pharmacological effects of composition of Examples and Comparative Examples on nephritis-induced renal failure model in rats.

The prostaglandin I derivative contained as an effective ingredient in the enhancing agent is represented by the Formula (I) described above.

Among the compounds represented by the above-described Formula (I), preferred are those wherein
$R^1$ is COOR$^2$,
wherein $R^2$ is hydrogen or a pharmaceutically acceptable cation,
A is
1) —(CH$_2$)$_m$— or
2) —CH$_2$—CH=CH—,
wherein in is an integer of 1 to 3,
Y is hydrogen,
B is —X—C($R^{11}$)($R^{12}$)O$R^{13}$,
wherein $R^{11}$ and $R^{13}$ are hydrogen, X is
1) —CH=CH—
2) —C≡C—, $R^{12}$ is
1) —Z—$Ar^2$
wherein Z is covalent bond, or straight or branched alkylene represented by $C_tH_{2t}$,
wherein t is an integer of 1 to 6, $Ar^2$ is phenyl, α-naphthyl, β-naphthyl, or phenyl or phenoxy-substituted phenyl, which phenyl or phenoxy-substituted phenyl is substituted with at least one chlorine, bromine, fluorine, iodine, trifluoromethyl, $C_1$-$C_4$ alkyl, nitro, cyano and methoxy, or
2) —Z—$R^3$
wherein Z represents the same meanings as described above, $R^3$ is $C_3$-$C_{12}$ cycloalkyl, or
3) —$C_uH_{2u}$—C≡C—$R^{17}$
wherein u is an integer of 1 to 7, $C_uH_{2u}$ is straight or branched alkylene, and $R^{17}$ is $C_1$-$C_6$ straight alkyl, the formula including d-isomers, l-isomers and racemic compounds.

Among the compounds represented by the above-described Formula (I), more preferred are those wherein
$R^1$ is COOR$^2$, wherein $R^2$ is hydrogen or a pharmaceutically acceptable cation,
A is —(CH$_2$)$_m$—, wherein m is an integer of 1 to 3,
Y is hydrogen,
B is X—C($R^{11}$)($R^{12}$)O$R^{13}$, wherein $R^{11}$ and $R^{13}$ are hydrogen,
X is —CH=CH—,
$R^{12}$ is —$C_uH_{2u}$—C≡C—$R^{17}$, wherein u is an integer of 1 to 7, $C_uH_{2u}$ is straight or branched alkylene, and $R^{17}$ is $C_1$-$C_6$ straight alkyl,
E is hydrogen or —$OR^{18}$, wherein $R^{18}$ is $R^2$ (wherein $R^2$ represents the same meanings as described above),
the formula including d-isomers, l-isomers and racemic compounds.

Specific examples include, but are not restricted to, such as beraprost of the formula below, as well as salts and esters thereof:

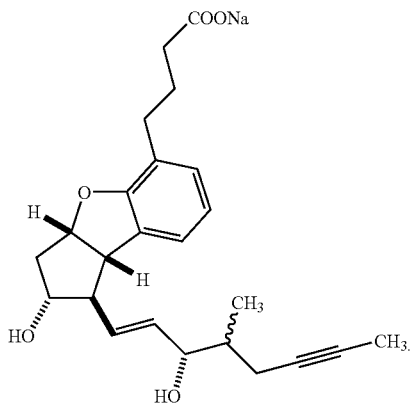

The compounds represented by the Formula (I) or salts thereof, especially beraprost sodium, are stable for a long time, and have high bioavailability when they are administered orally. In this respect, they are especially preferred for patients of renal diseases, especially chronic renal disease, because those patients are required to be administered for a long time.

The 4,8-inter-m-phenylene prostaglandin $I_2$ derivatives represented by the above-described Formula (I) are known in the art, and may be produced by known methods described in, for example, Japanese Patent Publication (Kokoku) No. 1-53672.

The 4,8-inter-m-phenylene prostaglandin $I_2$ derivatives represented by the above-described Formula (I) may be used individually or two or more of the derivatives may be used in combination.

In addition, the following compounds may be used as the prostaglandin I derivative: iloprost, epoprostenol sodium, carbacycin, cicaprost, eptaprost, ataprost, ciprostene, taprostene, clinprost, nileprost, naxaprostene, treprostinil, pimilprost, CS-570 (AsunoShinyaku, Apr. 24, 2003), TY-11223 (AsunoShinyaku, Apr. 24, 2003), TTC909 (AsunoShinyaku, Apr. 24, 2003), or OP-2507 (AsunoShinyaku, Apr. 24, 2003).

Moreover, the following prostaglandin I derivatives may be used: KP-10614, CH-5084, SC-43350, RS-93427, U-68215, RO-23-6416, CH-169, TEI-9063, AFP-07, cilo-prost, CS570, M-19791, Hoe892, R-59274, and CG4203.

Further, (16S)-15-deoxy-16-hydroxy-16-methyl-9(O)-methano-Δ6(9α)-prostaglandin $I_1$, 9(O)-methano-Δ6(9α)-prostaglandin $I_1$ methyl ester, 17(S),20-dimethyl-9(O)-methano-Δ6(9α)-prostaglandin $I_1$ methyl ester, 15R-isocarbacyclin derivatives described in Japanese Laid-open Patent Application (Kokai) No. 8-245498, and 15R-16-m-tolyl-17,18,19,20-tetranorisocarbacyclin and methyl ester thereof described in Japanese Patent Application No. 9-160320 may also be used.

Further, samixogrel (AsunoShinyaku, Apr. 24, 2003), BMY-42239 (AsunoShinyaku, Apr. 24, 2003), BMY-45778 (AsunoShinyaku, Apr. 24, 2003), and ONO-1301 (AsunoShinyaku, Apr. 24, 2003), which are reported to have similar activities to the prostaglandin 12, for example, the thrombocytic activity and vasodilation activity, as well as the compounds described in the EP0542203, EP0548959, EP0578847, EP0558062, EP0581187, WO9813356, Japanese Laid-open Patent Application (Kokai) No. 2000-191523, WO02/088084, and Japanese Patent No. 3245864 may also be used.

The renin-angiotensin system inhibitors which may be employed include ACE inhibitors, angiotensin II receptor antagonists, chymase inhibitors and renin inhibitors. Among these, ACE inhibitors and angiotensin II receptor antagonists are especially preferred.

The drugs which are broadly applied to clinical use and of which safety and efficacy on renal diseases have been shown are especially preferred.

Concrete examples of the ACE inhibitors which may be used are, but not restricted to, various low-molecular compounds as follows: enalapril maleate, alacepril, delapril, ramipril, captopril, lisinopril, benazepril hydrochloride, libenzapril, quinaprilat, imidapril hydrochloride, zofenopril calcium, fosinopril sodium, cilazapril, temocapril hydrochloride, spirapril hydrochloride, perindopril erbumine, moexipril hydrochloride, trandolapril, omapatrilat, ceronapril hydrate, idrapril, mixanpril, moveltipril calcium, rentiapril, utibapril, synecor, spiraprilat, zabicipril hydrochloride, E-4030 (Drug Data Report, Vol. 22, p 510, 2000), ceranopril, delapril, prentyl, ramapril, zofenopril, Sampatrilat, Pentopril, Libenzapril, Perindoprilat, Spiraprilat, BRL-36378 (N-[4-(2,3-Dihydrobenzofuran-2-yl)-1-(ethoxycarbonyl)butyl]-L-alanyl-L-proline), Zofenoprilat arginine, Fasidotril, MDL-100240 (4S,7S,12bR)-7-[2(S)-(Acetylsulfanyl)-3-phenylpropionamido]-6-oxo-1,2,3,4,6,7,8,12b-octahydropyrido[2,1-a][2]beizazepine-4-carboxylic acid, S-21402 (N-[2(S)-(Mercaptomethyl)-3(R)-phenylbutyl]-L-alanine), Gemopatrilat, AVE-7688 (CAS No473289-62-2: (4S,7S,12bR)-7-[2(S)-(Acetylsulfanyl)-3-methylbutyramido]-6-oxo-1,2,3,4,6,7,8,12b-octahydropyrido[2,1-a][2]benzazepine-4-carboxylic acid).

Among these, enalapril maleate, alacepril, delapril, ramipril, captopril, lisinopril, benazepril hydrochloride, libenzapril, utibapril, synecor, spiraprilat, zabicipril hydrochloride, quinaprilat, imidapril hydrochloride, zofenopril calcium, fosinopril sodium, cilazapril, temocapril hydrochloride, spirapril hydrochloride, perindopril erbumine, ceronapril hydrate, moexipril hydrochloride, trandolapril, idrapril, omapatrilat, Pentopril, Libenzapril, Perindoprilat, Spiraprilat, BRL-36378 (N-[4-(2,3-Dihydrobenzofuran-2-yl)-1-(ethoxycarbonyl)butyl]-L-alanyl-L-proline), Sampatrilat, Zofenoprilat arginine, Fasidotril, MDL-100240: (4S,7S,12bR)-7-[2(S)(Acetylsulfanyl)-3-phenylpropionamido]-6-oxo-1,2,3,4,6,7,8,12b-octahydropyrido[2,1-a][2]benzazepine-4-carboxylic acid, S-21402 (N-[2(S)-(Mercaptomethyl)-3(R)-phenylbutyl]-L-alanine), Gemopatrilat, AVE-7688 ((4S,7S,12bR)-7-[2(S)-(Acetylsulfanyl)-3-methylbutyramido]-6-oxo-1,2,3,4,6,7,8,12b-octahydropyrido[2,1-a][2]benzazepine-4-carboxylic acid) are preferred.

Especially, enalapril maleate, alacepril, delapril, ramipril, captopril, lisinopril, benazepril hydrochloride, libenzapril, quinaprilat, imidapril hydrochloride, zofenopril calcium, fosinopril sodium, cilazapril, temocapril hydrochloride, spirapril hydrochloride, perindopril erbumine, moexipril hydrochloride, trandolapril, omapatrilat, ceronapril hydrate, utibapril, and Sampatrilat are preferred.

As a matter of course, pharmaceutically acceptable salts of such compounds may also be used.

These ACE inhibitors are known in the art and may be produced by using known methods.

The angiotensin II receptor antagonists which may be used are the agents having activities to inhibit binding of angiotensin II to the angiotensin II receptor, especially its subtype AT1 receptor, on cell membrane competitively or noncompetitively, to attenuate the action of vasoconstriction and/or the action of proliferation of vascular smooth muscle, to alleviate hypertension.

The compounds having an antagonistic action against angiotensin II receptor used may be peptides or nonpeptides, but are preferably nonpeptides. Examples of the compounds having an antagonistic action against angiotensin II receptor include, but are not restricted to, the compounds as follows: losartan, eprosartan, candesartan cilexetil, valsartan, telmisartan, irbesartan, tasosartan, olmesartan medoxomil, EXP-3174 (Drug Data Report, Vol. 14, p 396, 1992), zolasartan, saprisartan, elisartan potassium, ripisartan, milfasartan, forasartan, embusartan, BMS-184698 (Drug Data Report, Vol. 16, p 449, 1994), 3-(2'-(tetrazol-5-yl)-1,1'-biphen-4-yl) methyl-5,7-dimethyl-2-ethyl-3H-imidazo[4,5-b]pyridine, BAY106734 (Drug Data Report, Vol. 18, p 518, 1996), BIBR363 (Drug Data Report, Vol. 18, p 139, 1996), CL329167 (2-butyl-6-(1-methoxy-1-methylethyl)-3-[2'(1H-tetrazol-5-yl)biphenyl-4-ylmethyl]quinazolin-4(3H)-one: Drug Data Report, Vol. 16, p 728, 1994), E4177 (3-(2'-caboxybiphenyl-4-ylmethyl)-2-cyclopropyl-7-methyl-3H-imidazo[4,5-b]pyridine or 4'-(2-cyclopropyl-7-methyl-3H-imidazo[4,5-b]pyridin-3-ylmethyl) biphenyl-2-carboxylic acid: Drug Data Report, Vol. 14, p 981, 1992), EMD73495, HN65021 (Drug Data Report, Vol. 16, p 914, 1994), HR720 (Drug Data Report, Vol. 17, p 147, 1995), HOE720, LRB081 (Drug Data Report, Vol. 16, p 1002, 1994), SC52458 (Drug Data Report, Vol. 15, p 632, 1993), SL910102, UP2696 (Drug Data Report, Vol. 16, p 1004, 1994), YM358 (2,7-diethyl-5-[2'-(1H-tetrazol-5-yl)biphenyl-4-ylmethyl]-5H-pyrazolo[1,5-b][1,2,4]triazole potassium salt monohydrate: Drug Data Report, Vol. 15, p 533, 1993), EMD66397, ME3221 (3-methoxy-2,6-dimethyl-4-[2'-(1H-tetrazol-5-yl)

biphenyl-4-ylmethoxy]pyridine: Drug Data Report, Vol. 16, p 636, 1994), TAK536 (2-ethoxy-1-[2'-(5-oxo-2,5-dihydro-1,2,4-oxadiazol-3-yl)biphenyl-4-yl)methyl]benzimidazol-7-carboxylic acid: Drug Data Report, Vol. 17, p 435, 1995), CGP42112A (Drug Data Report, Vol. 12, p 794, 1990), CGP49870, CP148130, E4188, EMD66684, EXP9954, FR1153332, GA0050, KT3579 (Drug Data Report, Vol. 15, p 631, 1993), LF70156, LRRB057 (Drug Data Report, Vol. 15, p 922, 1993), LY266099, LY301875 (Drug Data Report, Vol. 16, p 538, 1994), PD123177 (Drug Data Report, Vol. 13, p 123, 1994), PD126055 (Drug Data Report, Vol. 16, p 543, 1994), SC51757 (Drug Data Report, Vol. 16, p 453, 1994), SC54629 (Drug Data Report, Vol. 16, p 542, 1994), U96849, UK77778, WAY126227 (Drug Data Report, Vol. 15, p 1024, 1993), WK1260 (Drug Data Report, Vol. 15, p 635, 1993), WK1492, YH1498, and YM31472 (Drug Data Report, Vol. 15, p 1024, 1993), as well as Pomisartan, Olmesartan hydrate, KRH-594 (2-[[5-ethyl-3-[2'-(1H-tetrazol-5-yl)biphenyl-4-ylmethyl]-2,3-dihydro-1,3,4-thiadiazol-2-ylidene]aminocarbonyl]-1-cyclopentene carboxylic acid dipotassium salt), UR-7247 (3-isopropyl-1-propyl-5-[2'-(1H-tetrazol-5-yl)biphenyl-4-ylmethyl]-1H-pyrazol-4-carboxylic acid), EXP-3174 (2-butyl-4-chloro-1-[2'-(1H-tetrazolo-5-yl)biphenyl-4-ylmethyl]imidazol-5-carboxylic acid), L-159282 (N-[4'-(2-ethyl-5,7-dimethyl-3H-imidazo [4,5-b]pyridin-3-ylmethyl)biphenyl-2-sulfonyl]benzamide), CL-329167, DuP-532 (4-pentafluoroethyl-2-propyl-1-[2'-(1H-tetrazol-5-yl)biphenyl-4-ylmethyl]imidazol-5-carboxylic acid), ICI-D8731 (2-ethyl-4-[2'-(1H-tetrazol-5-yl)biphenyl-4-ylmethoxy]quinoline hydrochloride), ICI-D6888 (2-ethyl-4-[2'-(1H-tetrazol-5-yl)biphenyl-4-ylmethoxy]-5,6,7,8-tetrahydroquinoline hydrochloride), CI-996 (2-propyl-1-[2'-(1H-tetrazol-5-yl)biphenyl-4-ylmethyl]-4-[2-(trifluoroacetyl)pyrrol-1-yl]imidazol-5-carboxylic acid), and, in some cases, their metabolites (such as candesartan). As a matter of course, pharmaceutically acceptable salts of such compounds may also be used.

Among these, losartan, eprosartan, candesartan cilexetil, valsartan, telmisartan, irbesartan, tasosartan, olmesartan medoxomil, EXP-3174, zolasartan, saprisartan potassium, elisartan potassium, ripisartan, milfasartan, forasartan, embusartan, CL329167, E4177, ME3221, TAK536, Pomisartan, Olmesartan hydrate, KRH-594, UR-7247, EXP-3174, L-159282, CL329167, DuP-532, ICI-D8731, ICI-D6888, CI-996, and in some cases their metabolites (such as candesartan) are preferred. As a matter of course, pharmaceutically acceptable salts of such compounds may also be used.

Moreover, Losartan, Eprosartan, Candesartan cilexetil, Valsartan, Telmisartan, Irbesartan, Tasosartan, Olmesartan medoxomil, zolasartan, milfasartan, forasartan, and, in some cases, their metabolites (such as candesartan) as well as pharmaceutically acceptable salts thereof are especially preferred.

Nonpeptidic angiotensin II receptor antagonists are roughly classified according to their structures into biphenyl tetrazoles and non-biphenyl tetrazoles. The former include losartan, candesartan cilexetil and valsartan. On the other hand, the latter include eprosartan, zolasartan and telmisartan. Both types of the drugs may preferably be used as described in Examples.

These angiotensin II receptor antagonists are known in the art and may be produced by using known methods.

In addition, renin-angiotensin system inhibitors include chymase inhibitors. Chymase is a kind of serine proteases. It has been reported that chymase as well as ACE has an activity to convert angiotensin I into angiotensin II which has vasopressor activity, and that therefore there is a possibility to use selective inhibitors of chymase as antihypertensive drugs. Examples of low-molecular chymase inhibitors include 3-(2-naphthylcarbonyl)-5-[2-[5-[[(1-phenyl-1,2,3,4-tetrazolyl)-5z-thio]methyl]]furylmethylidene]-1,3-thiazolidine-2,4-dione, 3-(4-chlorobenzenesulfonyl)-1-(4-chlorophenyl)imidazolidine-2,4-dione, 3-(3-allyloxycarbonylmethylbenzenesulfon-yl)-1-phenyl-imidazolidine-2,4-dione and 7-[6-(6-biotinylaminocaproyl) aminocaproyl]amino-4-chloro-3-(2-phenylethoxy) isocoumarin. They are described in Japanese Laid-open Patent Application (Kokai) No. 2000-95770, WO98/09949, WO93-25574, U.S. Pat. No. 5,306,824, and WO96-4248.

As renin-angiotensin system inhibitors, compounds having renin-inhibiting activity are also preferred to use. Renin is a proteolytic enzyme secreted from juxtaglomerular cells of kidney, and converts angiotensinogen into angiotensin I in the renin-angiotensin system. Since angiotensin I is converted into angiotensin II, a strong pressure substance, in the body, renin-inhibiting substances may be used for treating hypertension. Therefore, it has been indicated that there is a possibility to use low-molecular compounds having renin-inhibiting activity as antihypertensive drugs. Concrete examples of the low-molecular compounds having renin-inhibiting activity include aliskiren, remikiren, and compounds described in Japanese Laid-open Patent Application (Kokai) No. 5-32602 such as (2S,3R,4S)-2-((2R)-2-(1-(4-morpholinylcarbonyl)methyl-N-(1-naphtylmethyl)amino) carbonylmethyl-4-methylpentionyl)amino-1-cyclohexyl-3,4-dihydroxy-6-methylheptane.

The renin-angiotensin system inhibitors mentioned above may be used individually or two or more inhibitors may be used in combination. The two or more renin-angiotensin system inhibitors belonging to different categories may also be used in combination.

In particular, it was reported recently that the progress of renal diseases was further delayed when ACE inhibitor and angiotensin II receptor antagonist were administered simultaneously (WO97/02032). Hence, administration of the prostaglandin I derivative in addition to the combination of both of ACE inhibitor and angiotensin II receptor antagonist can delay the progress of renal diseases with more certainty.

Conversely, to administer a renin-angiotensin system inhibitor to the patients of renal diseases to whom a prostaglandin I derivative is already administered is also very useful.

Renal diseases which may be prevented or treated include diabetic nephropathy, acute glomerulonephritis, chronic glomerulonephritis, nephrotic syndrome, lupus nephritis, interstitial nephritis, acute tubulointerstitial nephritis, chronic tubulointerstitial nephritis, acute renal failure and chronic renal failure. In addition, minimal change glomerulonephritis, focal/segmental glomerulonephritis, diffuse glomerulonephritis, mesangial proliferative glomerulonephritis, diffuse endocapillary proliferative glomerulonephritis, crescentic glomerulonephritis, diffuse scleraosing glomerulonephritis, and IgA nephritis, which are classified as chronic glomerulonephritis, may also be prevented or treated.

Moreover, an activity to suppress the decrease of renal function is exhibited by starting administration of the prostaglandin I derivatives even when the renal diseases reached more advanced stage, such as diabetic nephropathy with overt proteinuria and renal failure in the conservative stage, which shows elevation of serum creatinine level, on which renin-angiotensin inhibitors do not show sufficient effect.

The effect may be confirmed most clearly when the GFR (glomerular filtration rate) is used as an index, which is the most important index of the filtration function of the kidney. GFR may be evaluated by measuring clearance of creatinine or inulin. Alternatively, it may simply be estimated from blood creatinine level by using a conversion formula.

Blood creatinine and BUN (blood urea nitrogen) increase in accordance with decrease of renal function to filtrate low molecular substances, and therefore the effect to suppress renal damage may also be confirmed clearly by the serum creatinine or BUN level. In particular, the reciprocal of serum creatinine level decreases almost linearly with time. Thus, based on its slope, the depression rate of renal function may be estimated and the estimation is practiced clinically, for example, for evaluating the effect of adsorbent preparation in the renal failure stage (Biomater Artif Cells Immobilization Biotechnol. 1991; 19(1): 147-66, Am J Kidney Dis. 2003 March; 41 (3 Suppl 1): S35-7.).

These methods for evaluation based on creatinine are appropriate for the evaluation in the advanced stage of renal diseases where the elevation of creatinine is caused, i.e., in the renal failure stage, especially in the conservative stage.

In the case of nephropathy patients in earlier stage where the elevation of blood creatinine or BUN is not caused, the pharmacological effect may usually be evaluated based on the amount of urinary protein. Especially, in the case of evaluating diabetic nephropathy, the effect may be measured based on microalbumin in urine, from which earlier pathosis of the disease can be detected.

The dosage of the renin-angiotensin system inhibitors is preferably set to a dosage sufficient to obtain antihypertensive effect in each patient. On the other hand, the dosage of the prostaglandin I derivatives is preferably as high as possible to such an extent that the side effects are in acceptable levels. As shown, combination of the prostaglandin I derivatives and the renin-angiotensin system inhibitor shows a synergistic effect to suppress the progression of renal diseases, and therefore the combination of them allows the use of smaller doses of these drugs for suppressing the progression of renal diseases.

In particular, the side effects associated with vasodilation such as face flush, glow, headache dull, and palpitation, as well as the side effects such as digestive symptoms, including vomiting and diarrhea, and ache of jaw are caused when the dose of prostaglandin I derivatives is raised. Therefore, in the case where the use of high-dose is restricted, the dose of prostaglandin I derivatives may be reduced by virtue of the effect of this disclosure.

The renin-angiotensin system inhibitors are preferably administered at a dosage sufficient to exhibit antihypertensive activity. However, the synergistic effect allows use of a lower dosage.

Thus, it is expected that the side effects of ACE inhibitors such as dry cough, excessive decrease of pressure, strong vertigo or postural vertigo, hyperkalemia, angioedema, swelling of face, mouth or throat, and hepatopathy may be reduced. The temporary depression of renal function, especially hyperkalemia, observed in the beginning of administration of the drugs to the patients with renal failure, may also be reduced efficiently. Moreover, lightheadedness on standing due to excessive decrease of pressure, hyperkalemia, angioedema, swelling of face, mouth or throat, hepatopathy, and temporary depression of renal function, known as the side effects of angiotensin II receptor antagonists, may also be reduced efficiently.

When administered orally to an adult (50 kg of body weight), the dose of the renin-angiotensin system inhibitor is 0.01 to 1000 mg, preferably 0.1 to 100 mg in terms of the active compound, or prodrug or salt thereof as a single dose (1 unit of composition). It is desirable to administer the dose once to three times per day.

The dose of the prostaglandin I derivative, especially 4,8-inter-m-phenylene prostaglandin $I_2$ derivative, may be usually about 0.01 to 5000 μg, preferably 0.1 to 500 μg, as a single dose (1 unit of composition) when administered to an adult, and this dose is preferably administered about once to three times per day. Particularly, in the case of beraprost sodium, the dose to human patients of renal failure is preferably 0.02 to 500 μg and this dose is preferably administered twice to four times per day.

Formulation of the prostaglandin I derivative may be prepared by adding excipients such as starches, lactose, sucrose, glucose, mannitol, calcium carbonate and calcium sulfate; binders such as starches, dextrin, gum arabic, gum tragacanth, methyl cellulose, gelatin, polyvinyl pyrrolidone and polyvinyl alcohol; disintegrating agents such as starches, polyvinyl pyrrolidone and crystalline cellulose; lubricants such as magnesium stearate and talc; coloring agents, flavoring agents and so on.

The prostaglandin I derivative and the angiotensin system inhibitor in the form of separate formulations may be administered simultaneously or separately at different times. For convenience, they may be used as a kit containing both of the formulations or a kit of preparation containing both formulations in combination with a single drug. In particular, preparations of prostaglandin I derivatives and preparations of angiotensin system inhibitors often differs in respect of their usage and therefore administration of them is likely to be complicated. Therefore, such kits may be especially preferred to use. Moreover, the prostaglandin I derivative and the angiotensin system inhibitor may be administered in the form of a capsule containing granules of the both drugs.

Needless to say, depending on the characteristics of each drug, the release of each drug may be controlled individually so as to attain sustained or delayed release. Especially, to form prostaglandin I derivatives as a sustained release preparation leads to preferable results, because such preparation makes it possible to increase the dose of the prostaglandin I derivatives with higher safety.

The enhancing agent may be administered in various dosage forms. Specifically, when administered orally, the dosage form may be any conventional one, such as tablets, powders, fine granules, granules, tablets, solutions, syrups, capsules, pills and sprays. Preferably, the dosage form may be tablets, powders, fine granules, granules, tablets, solutions, syrups and capsules.

The enhancing agent may also be administered parenterally in the form of sterile solutions or the like. Sodium chloride, glucose or any other solute may be added to the solution, for example, in the amount sufficient to make the solution isotonic. In addition to the dosage form for oral administration mentioned above, the therapeutic and prophylactic agent may be prepared in various dosage forms, such as various types of injections and suppositories for parenteral administration. The formulation for oral and parenteral administration may be performed by conventional methods broadly used in the medical field.

The enhancing agent may be applied to not only human but also various animals such as mammals kept as pets.

Our compositions and methods will now be described concretely based on examples.

Example 1

To 9-week old WKY rats obtained from Charles River Japan, Inc., rabbit anti-rat glomerular basement membrane antiserum (NTS, 10-fold diluted, 3 mL/kg) was administered to induce nephritis. Two weeks later, urine and blood were collected, the animals were divided into the following 6 groups based on the protein level in urine and the blood creatinine level, and medication was started. At this time point, blood creatinine level had already been raised, so that the animals were judged as in the renal failure stage. Evaluation of the renal function was based on the blood creatinine level.
1) Control Group: solvent alone was administered, n=6
2) BPS100 Group (Comparative Example): beraprost sodium 100 μg/kg (BID: this dose was administered twice a day), n=6
3) BPS300 Group (Comparative Example): beraprost sodium 300 μg/kg (BID), n=6
4) Candesartan10 Group (Comparative Example): candesartan cilexetil 10 mg/kg (OAD: this dose was administered once a day), n=6
5) Candesartan30 Group (Comparative Example): candesartan cilexetil 30 mg/kg (OAD), n=6
6) BPS100+Candesartan10 Group (this disclosure): beraprost sodium 100 μg/kg (BID)+candesartan cilexetil 10 mg/kg (OAD), n=7

After the start of the medication, blood was collected at one week intervals, and blood creatinine level was measured. The results are shown in FIG. 1.

As shown in FIG. 1, in the BPS100 group and candesartan10 group, almost no difference in the effect to suppress the progress of nephritis was observed when compared with the control group. On the other hand, in the BPS100+ candesartan10 group in which both of the drugs were administered, the raise in the blood creatinine level was almost completely inhibited after the administration of the drugs. On the other hand, even if the dosage of each drug was increased (candesartan30 group and BPS300 group), the effect to suppress the progress of nephropathy was smaller than that observed in BPS100+candesartan10 group.

Thus, by administering BPS and candesartan cilexetil in low dosages at which each drug did not suppress the progress of the renal disease when administered individually, the effect of suppressing progress of the renal failure was drastically promoted even when compared to the cases where each drug was administered individually at a higher dosage. These results suggest the excellent usefulness of the combination drug containing the two drugs.

During the experiments, since the $PGF_{1\alpha}$ level in urine was not changed by the administration of candesartan, it was confirmed that there was no possibility that the increase in the endogenous prostaglandin $I_2$ production contributed to the phenomenon. Further, plasma fibrinogen level was measured, but no difference was observed between different groups.

Example 2

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC (OAD)+distilled water (BID), n=6
2) Telmisartan Group (Comparative Example): telmisartan 40 mg/kg (OAD)+distilled water (BID), n=5
3) BPS Group (Comparative Example): 0.5% CMC (OAD)+beraprost sodium 100 μg/kg (BID), n=5
4) Telmisartan+BPS Group (this disclosure): telmisartan 40 mg/kg (OAD)+beraprost sodium 100 μg/kg (BID), n=6

As shown in Table 1, in the BPS group, almost no difference in the effect to suppress the progress of renal failure was observed when compared with the control group. In the telmisartan group and telmisartan+BPS group, the progress of renal failure was suppressed, and this suppressive effect was stronger in the telmisartan+BPS group. On the other hand, when blood creatinine level was measured again at one week after the end of the medication, renal failure was progressed in the telmisartan group, while blood creatinine level of the animals in the telmisartan+BPS group was suppressed to about the same degree as that of normal animals. Thus, in the combination group, blood creatinine level was reduced rather than increased even after the end of the medication. These results suggest the excellent usefulness of combined medication.

TABLE 1

| Group | blood creatinine level at 7 weeks after induction (mg/dL) | blood creatinine level at 8 weeks after induction (1 week after the end of the medication) (mg/dL) |
|---|---|---|
| Control | 1.79 ± 0.37 | |
| Telmisartan | 0.93 ± 0.43 | 1.18 ± 0.80 |
| BPS | 1.56 ± 0.76 | |
| Telmisartan + BPS | 0.61 ± 0.09 | 0.29 ± 0.01 | mean ± S.E.

Example 3

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC (BID)+distilled water (BID), n=6
2) Losartan Group (Comparative Example): losartan 30 mg/kg (BID)+distilled water (BID), n=5
3) BPS Group (Comparative Example): 0.5% CMC (BID)+beraprost sodium 100 μg/kg (BID), n=6
4) Losartan+BPS Group (this disclosure): losartan 30 mg/kg (BID)+beraprost sodium 100 μg/kg (BID), n=5

At six weeks after the induction, blood creatinine level was measured to assess the progress of renal failure. As shown in Table 2, in the losartan group and BPS group, no difference in the effect to suppress the progress of renal failure was observed at the dosage used herein when compared with the control group. On the other hand, in the losartan+BPS group in which both of the drugs were administered, the progress of renal failure was significantly suppressed when compared with the control group (p<0.05). Thus, by the combined administration of BPS and losartan which is an ARB in low dosages at which each drug did not show the effect when administered individually, the remarkable effect of suppressing progress of renal failure could be obtained.

TABLE 2

| Group | blood creatinine level at 6 weeks after induction (mg/dL) |
|---|---|
| Control | 1.83 ± 0.47 |
| Losartan | 1.94 ± 0.61 |
| BPS | 0.93 ± 0.18 |
| Losartan + BPS | 0.65 ± 0.13* | mean ± S.E.
*$p < 0.05$, when compared with the control group (t-test)

Example 4

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC(OAD)+distilled water (BID), n=6
2) Enalapril Group (Comparative Example): enalapril maleate 10 mg/kg (OAD)+distilled water (BID), n=5
3) BPS Group (Comparative Example): 0.5% CMC (OAD)+beraprost sodium 100 μg/kg (BID), n=6
4) Enalapril+BPS Group (this disclosure): enalapril maleate 10 mg/kg (OAD)+beraprost sodium 100 μg/kg (BID), n=6

After the start of the medication, blood was collected at one week intervals, and blood creatinine level was measured. The data were plotted taking the reciprocal of the blood creatinine level measured for five weeks after the start of the medication along the ordinate and taking the time along the abscissa, and the slope of the regression line was defined as the rate of progress of renal failure of each animal. The results are shown in Table 3.

As shown in Table 3, in the enalapril group and BPS group, no difference in the effect to suppress the progress of renal failure was observed at the dosage used herein when compared with the control group. On the other hand, in the enalapril+BPS group in which both of the drugs were administered, the progress of renal failure was significantly suppressed when compared with the control group ($p<0.05$). Thus, by combined administration of BPS and ACE inhibitor enalapril in low dosages at which each drug did not show the effect when administered individually, the remarkable effect of suppressing progress of renal failure could be obtained.

TABLE 3

| Group | rate of progress of renal failure (dL/mg × week) | blood creatinine level at 6 weeks after induction (mg/dL) |
|---|---|---|
| Control | 0.41 ± 0.04 | 1.83 ± 0.47 |
| Enalapril | 0.41 ± 0.04 | 1.83 ± 0.44 |
| BPS | 0.32 ± 0.04 | 0.93 ± 0.18 |
| Enalapril + BPS | 0.24 ± 0.05* | 0.60 ± 0.08 | mean ± S.E.
*$p < 0.05$, when compared with the control group (t-test)

Example 5

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC(OAD)+distilled water (BID), n=6
2) Lisinopril Group (Comparative Example): lisinopril 10 mg/kg (OAD)+distilled water (BID), n=5
3) BPS Group (Comparative Example): 0.5% CMC (OAD)+beraprost sodium 100 μg/kg (BID), n=5
4) Lisinopril+BPS Group (this disclosure): lisinopril 10 mg/kg (OAD)+beraprost sodium 100 μg/kg (BID), n=6

After the start of the medication, blood was collected at one week intervals, and blood creatinine level was measured. The data were plotted taking the reciprocal of the blood creatinine level measured for five weeks after the start of the medication along the ordinate and taking the time along the abscissa, and the slope of the asymptote was defined as the rate of progress of renal failure of each animal. The results are shown in Table 4.

As shown in Table 4, in the lisinopril group and BPS group, almost no difference in the effect to suppress the progress of renal failure was observed when compared with the control group. On the other hand, in the lisinopril+BPS group in which both of the drugs were administered, the progress of renal failure was significantly suppressed when compared with the control group ($p<0.05$).

TABLE 4

| Group | rate of progress of renal failure (dL/mg × week) | blood creatinine level at 6 weeks after induction (mg/dL) |
|---|---|---|
| Control | 0.43 ± 0.02 | 1.49 ± 0.41 |
| Lisinopril | 0.39 ± 0.08 | 1.20 ± 0.34 |
| BPS | 0.37 ± 0.07 | 1.49 ± 0.59 |
| Lisinopril + BPS | 0.27 ± 0.05* | 0.81 ± 0.32 | mean ± S.E.
*$p < 0.05$, when compared with the control group (Wilcoxon test)

Example 6

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC(OAD)+distilled water (BID), n=6
2) Perindopril Group (Comparative Example): perindopril erbumine 10 mg/kg (OAD)+distilled water (BID), n=6
3) BPS Group (Comparative Example): 0.5% CMC (OAD)+beraprost sodium 100 μg/kg (BID), n=6
4) Enalapril+BPS Group (this disclosure): perindopril erbumine 10 mg/kg (OAD)+beraprost sodium 100 μg/kg (BID), n=6

After the start of the medication, blood was collected at one week intervals, and blood creatinine level was measured. The data were plotted taking the reciprocal of the blood creatinine level measured for six weeks after the start of the medication along the ordinate and taking the time along the abscissa, and the slope of the asymptote was defined as the rate of progress of renal failure of each animal. The results are shown in Table 5.

As shown in Table 5, tendency to suppress the progress of renal failure was observed in the perindopril group and BPS group when compared with the control group. Moreover, in the perindopril+BPS group in which both of the drugs were administered, strong tendency to suppress the progress of renal failure was observed when compared with the control group.

TABLE 5

| Group | rate of progress of renal failure (dL/mg × week) | blood creatinine level at 6 weeks after induction (mg/dL) |
| --- | --- | --- |
| Control | 0.35 ± 0.04 | 1.45 ± 0.32 |
| Perindopril | 0.30 ± 0.05 | 1.09 ± 0.42 |
| BPS | 0.29 ± 0.03 | 0.93 ± 0.18 |
| Perindopril + BPS | 0.21 ± 0.07 | 0.75 ± 0.16 |

Example 7

To 9-week old WKY rats, rabbit anti-rat glomerular basement membrane antiserum was administered to induce nephritis. At two weeks after administering the antiserum, the animals were divided into the following 4 groups and medication was started.
1) Control Group: 0.5% CMC(OAD)+distilled water (BID), n=11
2) Candesartan Group (Comparative Example): candesartan cilexetil 10 mg/kg (OAD)+distilled water (BID), n=11
3) BPS Group (Comparative Example): 0.5% CMC (OAD)+beraprost sodium 100 μg/kg (BID), n=11
4) Candesartan+BPS Group (this disclosure): candesartan cilexetil 10 mg/kg (OAD)+beraprost sodium 100 μg/kg (BID), n=12

Figure 2:
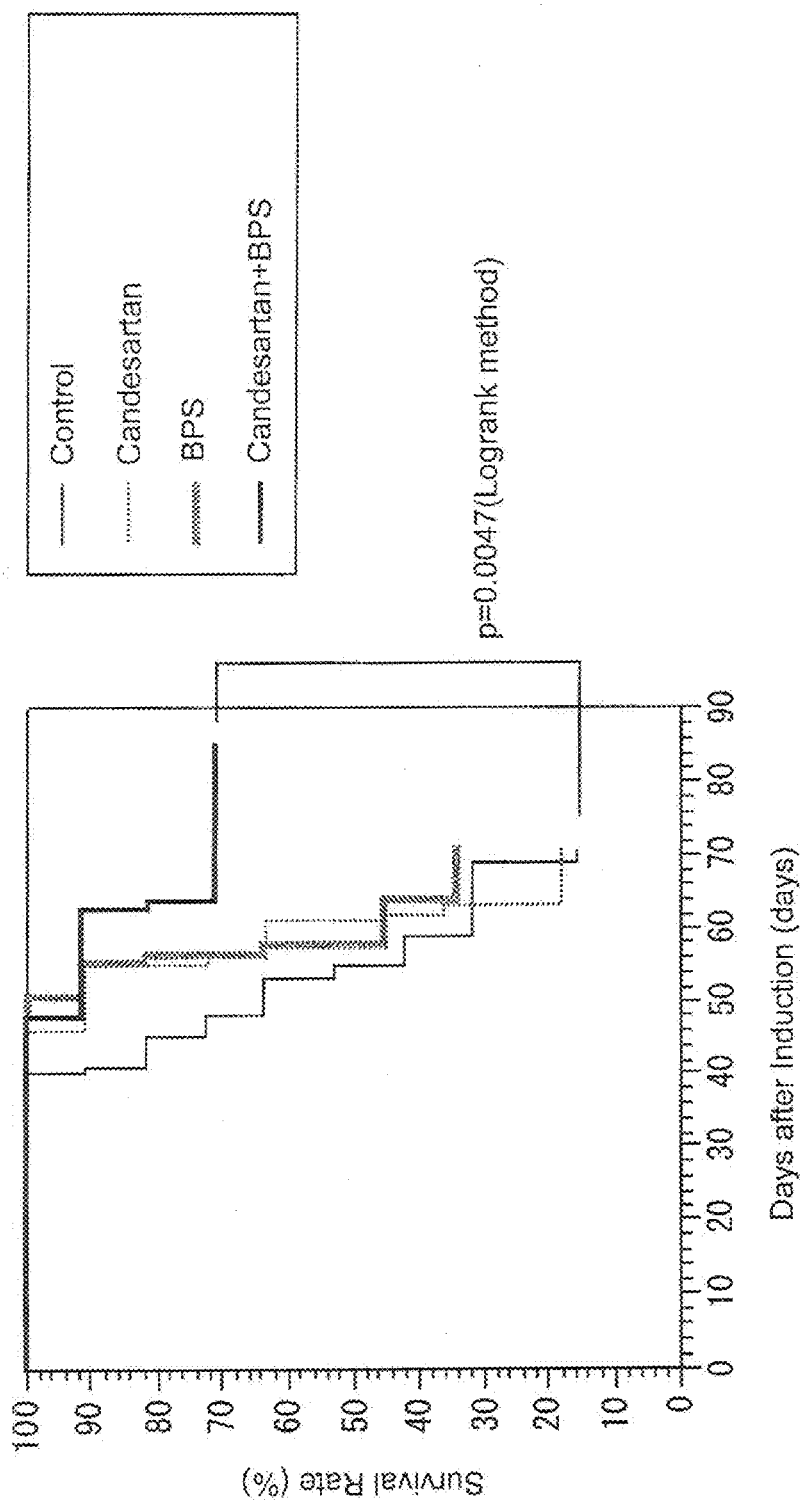
FIG. 2 shows pharmacological effects of composition of Examples and Comparative Examples on nephritis-induced renal failure model in rats.

As shown in FIG. 2, in the candesartan group and BPS group, no difference in the mortality rate was observed at the dosage used herein when compared with the control group. On the other hand, in the candesartan+BPS group in which both of the drugs were administered, the survival rate was significantly improved when compared with the control group ($p<0.05$). Thus, by combined administration of candesartan which is an ARB and BPS in low dosages at which each drug did not show the effect when administered individually, the remarkable effect of improving mortality caused by renal failure was observed.

The invention claimed is:

1. A method of treating chronic renal failure comprising administering an angiotensin II receptor antagonist and a therapeutic agent for chronic renal failure comprising as an effective ingredient beraprost or a pharmaceutically acceptable salt or ester thereof, to a patient suffering from chronic renal failure that is in the conservative stage which shows an elevated serum creatinine level.

2. The method according to claim 1, wherein the angiotensin II receptor antagonist is selected from the group consisting of losartan, valsartan, telmisartan, irbesartan, olmesartan medoxomil, candesartan, and their pharmaceutically acceptable salts.

3. The method according to claim 1, wherein the method suppresses an elevation of serum creatinine with time during chronic renal failure.

4. The method according to claim 1, wherein the method suppresses a sequential decrease in the reciprocal of serum creatinine with time.

5. The method according to claim 1, wherein the method suppresses a decrease in the glomerular filtration rate with time during chronic renal failure.

6. The method of claim 1, wherein the angiotensin II receptor antagonist is Candesartan or Candesartan Cilexetil or a pharmaceutically acceptable salt thereof.

* * * * *